United States Patent [19]

Narishige et al.

[11] Patent Number: 4,526,169

[45] Date of Patent: Jul. 2, 1985

[54] FINE CONTROL SYSTEM FOR A GLASS ELECTRODE OR THE LIKE

[75] Inventors: Eiichi Narishige; Shinji Yoneyama, both of Tokyo, Japan

[73] Assignee: Narishige Scientific Instrument Laboratory, Ltd., Japan

[21] Appl. No.: 511,002

[22] Filed: Jul. 5, 1983

[30] Foreign Application Priority Data

Feb. 21, 1983 [JP] Japan ................... 58-27478

[51] Int. Cl.³ .............................................. A61B 17/36
[52] U.S. Cl. .................................. 128/303 B; 60/581;
60/567; 60/594; 604/116
[58] Field of Search ............. 128/303 B; 60/581, 567,
60/594; 604/116, 117

[56] References Cited

U.S. PATENT DOCUMENTS 2,300,675 11/1942 Jones .................................. 60/594 X
3,363,418 1/1968 Hebel et al. ........................... 60/567
4,194,437 3/1980 Rosleim ............................ 60/567 X
4,342,951 8/1982 Muller et al. ................ 128/303 B X

FOREIGN PATENT DOCUMENTS 482439 1/1970 Switzerland ................... 128/303 B Primary Examiner—Edward M. Coven
Attorney, Agent, or Firm—Cushman, Darby & Cushman

[57] ABSTRACT

An improved system for finely and precisely controlling the operational position of a glass electrode, micropipette, micro surgical knife or the like with the aid of hydraulic remote control devices including hydraulic hoses is disclosed. This system includes a control stand with an actuator assembly firmly mounted thereon, said actuator assembly comprising X-, Y- and Z-coordinate actuators, a first fine adjusting device for roughly adjusting the X- and Y-coordinate actuators and a second fine adjusting device for adjusting the Z-coordinate actuator and moreover finely adjusting the X- and Y-coordinate actuators. A glass electrode or the like to be finely located is adjustably mounted on the actuator assembly. The first fine adjusting device comprises two fine adjusting handle devices adapted to adjust hydraulic pressure in a hydraulic chamber by turning a handle with operator's fingers and adjusted hydraulic pressure is transmitted to both the X- and Y-coordinate actuators on the control stand so as to effect rough positioning. The second fine adjusting device includes a micrometer head with a number of calibrations engraved thereon so that the Z-coordinate actuator is adjusted by turning the handle of the micrometer head and both the X- and Y-coordinate actuators are finely adjusted by swing movement of the whole micrometer head about the center of a movable ball.

10 Claims, 4 Drawing Figures

FINE CONTROL SYSTEM FOR A GLASS ELECTRODE OR THE LIKE

BACKGROUND OF THE INVENTION

1. Field of the Invention

The present invention relates to a fine control system for a glass electrode or the like and more particularly to an improved system for finely and precisely controlling the position of a glass electrode, micropipette, micro surgical knife or the like fundamentally for the field of medical science with the aid of hydraulic remote control devices.

2. Description of the Prior Art

In recent years a glass electrode having a diameter dimensioned in the range of 1 to 3 mm and a length dimensioned in the range of 50 and 60 mm has been developed for the above-mentioned fundamental field of medical science. The interior of the glass electrode is filled with electrolyte and its foremost end part is reduced in diameter in order of 0.1 micron in the form of an injector needle. As is well known, development of the glass electrode as described above makes it possible to medically examine and research the inside structure of a certain cell by inserting the glass electrode thereinto.

When a glass electrode having a diameter of 0.1 micron at the foremost end thereof is to be inserted into a certain cell, it is necessary to precisely locate the glass electrode so as not to damage or injure not only a cell to be examined but also the glass electrode itself. Moreover, fine control of the positioning, thereof without any occurrence of deviation, snake movement or the like is also required.

To precisely locate the position of a glass electrode or the like a hitherto known apparatus is typically constructed such that an actuating mechanism is provided for each of three directions of X-, Y- and Z-coordinates so as to displace the glass electrode or the like by a required distance by rotating a handle on each of the actuating mechanisms with the operator's hands. Since the conventional apparatus is operated directly with the operator's hands, a problem arises that vibratory movement of the operator's hand tends to be transmitted to the glass electrode or the like and is amplified during transmission. In view of the problem, there is a necessity for inhibiting vibratory movement caused by manual handling as far as possible before inserting into a certain cell a glass electrode having a foremost end part dimensioned in a diameter range of 10 to 20 microns. Therefore, the insertion operation of the glass electrode should be performed with critical caution and extremely high skill. Further, another problem with respect to the conventional apparatus that has been noted is that the glass electrode tends to be disengaged from a cell when operator's hand is removed from the handle on the apparatus after it has been inserted therein leading to a disadvantage that continuous examination and recording work cannot be performed.

To obviate the problems with the conventional apparatus several proposals have been suggested. An apparatus in accordance with a typical proposal is constructed in such a manner that a hydraulic cylinder is provided for each of three directions of X-, Y- and Z-coordinates in which a piston is slidably disposed and a hydraulic chamber is formed in the space defined by the end wall of a cylinder. A rolling diaphragm is attached to the rear end of the piston and the hydraulic chamber is in operative connection with a control handle by way of hydraulic hose. Thus, fine and precise locating of a glass electrode with the aid of a hydraulic system is assured in the three coordinate directions without any transmittance of vibratory movement caused by the operator's hands.

SUMMARY OF THE INVENTION

The present invention is concerned with an improvement relating to the above-proposed fine control system for a glass electrode or the like with the aid of hydraulic pressure and a characterizing feature of the invention consists in that X- and Y-coordinate actuators in an actuator assembly on a control stand comprising three X-, Y- and Z-coordinate actuators are roughly adjusted by means of a first fine adjusting device, the Z-coordinate actuator is then adjusted by means of a second fine adjusting device and thereafter the X- and Y-coordinate actuators are finely adjusted by way of swing movement of a micrometer head on the second fine adjusting device.

The control stand with the actuator assembly mounted thereon is firmly held on a holder arm standing upright on the base so that the X-, Y- and Z-coordinate actuators are assembled one above another with angular displacement of 90 degrees relative to the adjacent one. A glass electrode or the like is fixedly supported on the uppermost actuator.

The first fine adjusting device constituting an essential component of the present invention for roughly adjusting both the X- and Y-coordinate actuators includes two sets of fine adjusting handle devices which are in operative connection with the actuators via hydraulic hoses. Each of the fine adjusting handle devices comprises a handle with a number of calibrations engraved thereon and a rod adapted to move back and forth as the handle is rotated, the rod having a flexible diaphragm attached to the fore end part thereof, and a hydraulic chamber defined in the space between the end wall of a cylinder and the diaphragm. The hydraulic chamber is in communication with a hydraulic chamber in a corresponding actuator on the control stand via a hydraulic hose and is also in communication with a hydraulic chamber in a corresponding actuator in the second fine adjusting device.

The second fine adjusting device constituting another essential component of the invention for adjusting the Z-coordinate actuator and finely adjusting the X- and Y-coordinate actuators includes a cylindrical box, a Y-coordinate actuator fixedly mounted on the base at the central part of the cylindrical box to actuate in the horizontal direction, and an X-coordinate actuator fixedly mouned on the Y-coordinate actuator at a right angle relative to the direction of actuation of the latter to actuate in the horizontal direction, a ball attached to the uppermost end of a support rod standing upright on the X-coordinate actuator. A movable ball having a through hole formed therein in the vertical direction is provided so as to receive the stationary ball on the support rod with a close clearance kept therebetween. The movable ball is turnable by an angular distance of 360 degrees as seen from the above and moreover is inclinable by a certain angle as seen in a vertical sectional plane. A micrometer head device having a lower male threaded part is screw-fitted into the upper female threaded part of the through hole in the movable ball. The X-coordinate actuator is in operative connection with the X-coordinate actuator in the actuator assembly on the control stand via one of the fine adjusting handle devices and a hydraulic hose, whereas the Y-coordinate actuator is also in operative connection with the Y-coordinate actuator in the actuator assembly via the other fine adjusting handle device and a hydraulic hose.

The micrometer head device for controlling actuation of the Z-coordinate actuator in the actuator assembly is constructed in the substantially same manner as the fine adjusting handle in the first fine adjusting device and includes a sleeve casing with a male threaded part formed at the lower end thereof. A micrometer head is rotatably fitted onto the sleeve casing with a number of calibrations engraved on the periphery thereof. A screw spindle is adapted to be displaced up and down as the micrometer head is rotated, the screw spindle having a flexible diaphragm attached to the lower end part thereof. A hydraulic chamber defined in the space between the end wall of the sleeve casing and the diaphragm is provided, the hydraulic chamber being in communication with a hydraulic chamber in the Z-coordinate actuator in the actuator assembly via a hydraulic hose. Thus, actuation of the Z-coordinate actuator can be controlled by rotating the micrometer head. Further, the X- and Y-coordinate actuators in the second fine adjusting device are finely adjusted by way of swing movement of the micrometer head device inclined about the center of the movable ball by a certain angle so that variation in hydraulic pressure caused by the swing movement is transmitted to both the X- and Y-actuators in the actuator assembly so as to finely adjust actuation of the latter whereby a glass electrode or the like is precisely located as required.

To change an inclination angle of the micrometer head device, (i.e., an extent of fine adjustment) an arrangement is made so as to change height difference between the center of the movable ball and the center of the stationary ball. Specifically, a turn table with the micrometer head device mounted thereon is screw-fitted onto the upper male threaded part of the cylindrical box and therefore the height difference therebetween can be determined as required by turning the turn table by a certain angle in the selected direction.

The turn table has a recessed part formed at the central area thereof and a male threaded part of a tightening bush is screw-fitted into a female threaded part of the recess so that the movable ball is rotatably contained in the space defined by a combination of the tightening bush and the recessed part of the turn table. Thus, tightness of swing movement of the micrometer head device can be selectively determined by adjusting the extent of turning of the tightening bush.

Each of the X-, Y- and Z-coordinate actuators on the control stand comprises a slide having an inverted U-shaped cross-sectional configuration, a cylinder member disposed in said slide so as to move in the longitudinal direction, a rod attached to a bracket at the one end of the slide to protrude into the interior of the cylinder member in the axial direction and a flexible diaphragm secured to the fore end part of said rod and liquid-tightly attached to the inner wall of the cylinder member so as to define a hydraulic chamber in the space between the end wall of the cylinder member and the diaphragm. As variation in hydraulic pressure in the first and second fine adjusting devices is transmitted to the hydraulic chamber, the diaphragm is caused to expand or contract and thereby the rod is displaced forward or backward whereby actuation of the actuator is controlled as required.

The X- and Y-coordinate actuators in the second fine adjusting device are adapted to be controlled by way of swing movement of the micrometer head device and are preferably constructed in the same manner as those of the actuator assembly on the control stand.

Hence, it is an object of the present invention to provide an improved system for finely and precisely controlling the position of a glass electrode or the like which assures that control operation is carried out without any adverse affect caused by deviation, vibratory movement or the like which is attributable mainly to the manual handling by an operator.

It is another object of the present invention to provide an improved system for finely and precisely controlling the position of a glass electrode or the like which assures fine control operation at any position located remote from a control stand on which a glass electrode or the like is fixedly carried together with an actuator assembly.

It is another object of the present invention to provide an improved system for finely and precisely controlling the position of a glass electrode or the like which assures that the glass electrode or the like is exactly located at the required position.

It is still another object of the present invention to provide an improved system for finely and precisely controlling the position of a glass electrode or the like which has no fear of causing disconnection or deviation of the glass electrode or the like after the latter has been located at a predetermined position.

Other objects, features and advantages of the present invention will become more clear from a reading of the following description in conjunction with the accompanying drawings.

BRIEF DESCRIPTION OF THE DRAWINGS

The accompanying drawings will be briefly described below.

DETAILED DESCRIPTION OF THE PREFERRED EMBODIMENT

The present invention will now be described in greater detail below with reference to the accompanying drawings which illustrate an embodiment of the invention.

Figure 1:
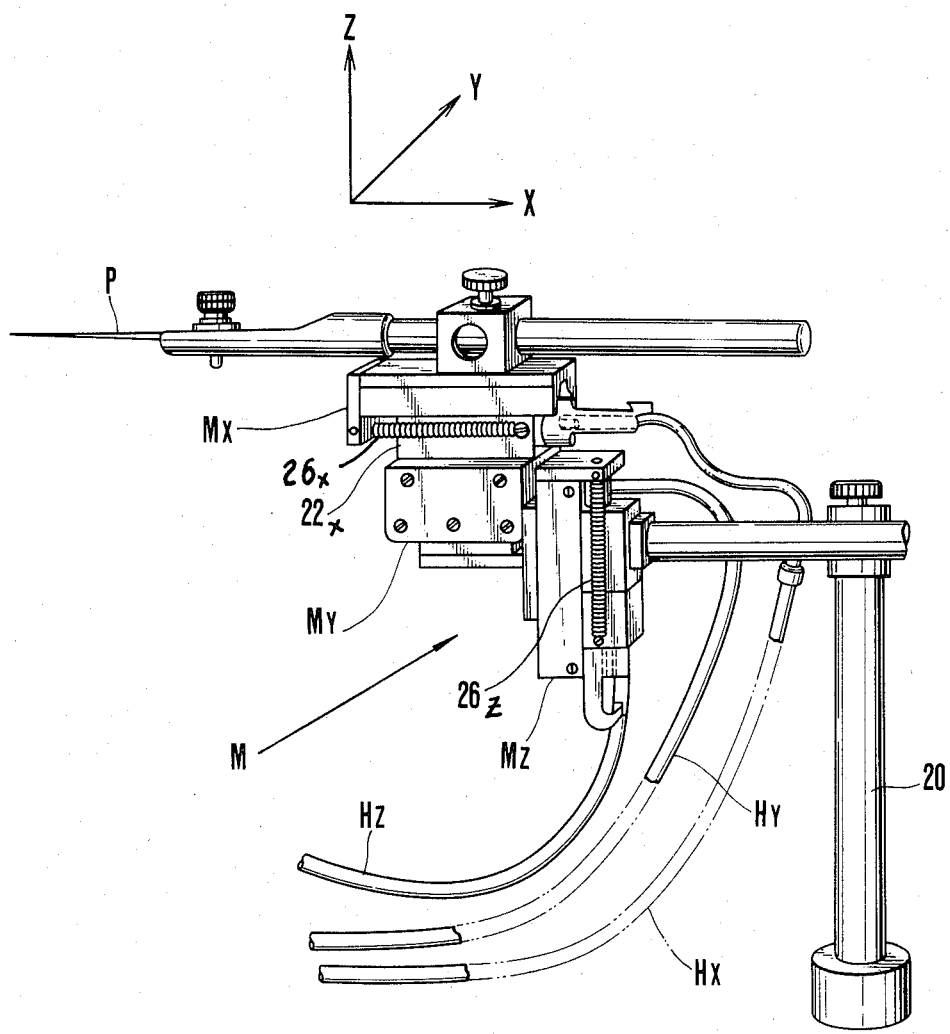
FIG. 1 is a perspective view illustrating a system for finely controlling the position of a glass electrode in accordance with a preferred embodiment of the present invention.

Referring first to FIG. 1, a control stand with a glass electrode P mounted thereon is identified with reference letter M. In the drawing reference numeral 20 designates a vertically extending holder arm by means of which the control stand M is firmly mounted on a base (not shown). As will be apparent from the drawing, sliding movement in the direction of each of the X, Y and Z coordinates with respect to the holder arm 20 as a reference axis is carried out by means of slave actuators $M_x$, $M_y$, $M_z$ which are arranged in operative association relative to one another.

The glass electrode P is attached to the slave actuator $M_x$ with the aid of a set screw so that it is displaced in the three directions in conformance with operation of each of the actuators.

Figure 3:
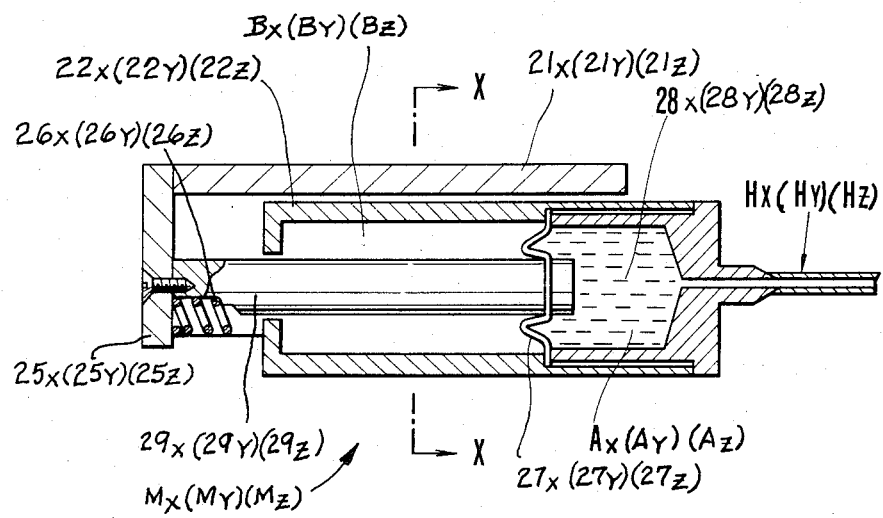
FIG. 3(a) is a longitudinal sectional view of an actuator for positioning operation in each of X, Y and Z coordinates.
FIG. 3(b) is a cross-sectional view of the actuator taken along line X—X in FIG. 3(a).
Figure 3:
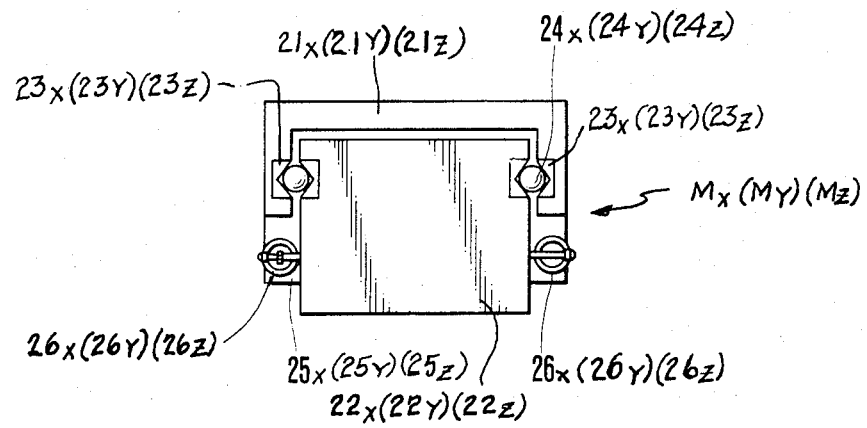

The structure of the master actuator is illustrated in FIGS. 3(a) and (b). Only slave actuator $M_x$ is shown in FIGS. 3(a) and 3(b) and is representative of the structure of slave actuators $M_y$ and $M_z$. Thus, for the discussion which follows, reference numerals for slave actuators $M_y$ and $M_z$ are parenthetically indicated beside corresponding reference numerals for slave actuator $M_x$. As shown in FIGS. 3(a) and 3(b), slave actuator $M_x$ includes a slide $21_x$ ($21_y$) ($21_z$) having an inverted U-shaped cross-sectional configuration and a cylinder member $22_x$ ($22_y$) ($22_z$) adapted to move in said slide 21 with the aid of guiding given thereby respectively.

As is best seen in FIG. 3(b), the slide $21_x$ ($21_y$) ($21_z$) has grooved rails $23_x$ ($23_y$) ($23_z$) fitted into both the inside walls, while the cylinder member $22_x$ ($22_y$) ($22_z$) has the same grooved rails $23_x$ ($23_y$) ($23_z$) fitted into the outside walls. The grooved rails $23_x$ ($23_y$) ($23_z$) are made of hard metallic material such as stainless steel or the like. A number of steel balls $24_x$ ($24_y$) ($24_z$) are disposed in the grooves on the rails $23_x$ ($23_y$) ($23_z$) are sandwiched therebetween whereby both the members are relatively displaced very smoothly. Between a bracket $25_x$ ($25_y$) ($25_z$) fixed to the one end of the slide $21_x$ ($21_y$) ($21_z$) and the cylinder member $22_x$ ($22_y$) ($22_z$) are disposed a pair of expansive coil springs $26_x$ ($26_y$) ($26_z$) of which one end is secured to the bracket $25_x$ ($25_y$) ($25_z$) and of which the other end is secured to the cylinder member $22_x$ ($22_y$) ($22_z$) so that the slide $21_x$ ($21_y$) ($21_z$) moves against the resilient force of the coil springs $26_x$ ($26_y$) ($26_z$). The cylinder member $22_x$ ($22_y$) ($22_z$) is constructed of two components and a flexible diaphragm $27_x$ ($27_y$) ($27_z$) made of cloth lined with synthetic rubber in a cap-shaped cross-sectional configuration is sandwiched between the two components in the illustrated manner so as to divide the inside space of the cylinder member $22_x$ ($22_y$) ($22_z$) into two parts, one of them being a hydraulic chamber $A_x$($A_y$)($A_z$) which is filled with petroleum based hydraulic oil 28 and the other one being an empty $B_x$($B_y$)($B_z$). As hydraulic pressure is introduced into the hydraulic chamber $A_x$($A_y$)($A_z$) of the actuator via a hydraulic hose $H_x$($H_y$)($H_z$), the diaphragm $27_x$($27_y$)($27_z$) is caused to expand from the illustrated state under the influence of hydraulic pressure and thus a rod $29_x$($29_y$)($29_z$) secured to the bracket $25_x$($25_y$)($25_z$) of the slide $21_x$($21_y$)($21_z$) by means of a set screw is thrusted in the leftward direction as seen in the drawing FIG. 3(a). As a result, the slide $21_x$($21_y$)($21_z$) moves leftward away from the cylinder member $22_x$($22_y$)($22_z$) against the resilient force of the coil springs $26_x$($26_y$)($26_z$). Next, when hydraulic pressure is released from the hydraulic chamber $A_x$, ($A_y$)($A_z$) the slide $21_x$($21_y$)($21_z$) is restored to the original position. Thus, the control stand M is constructed by assembling the slave actuators $M_x$, $M_y$ and $M_z$ in such a manner as illustrated in FIG. 1.

Next, a fine adjusting device MH will be described below with reference to FIG. 2. The fine adjusting device MH is in hydraulic communication with the slave actuators $M_x$, $M_y$ and $M_z$ via hydraulic hoses $H_x$, $H_y$ and $H_z$.

Figure 2:
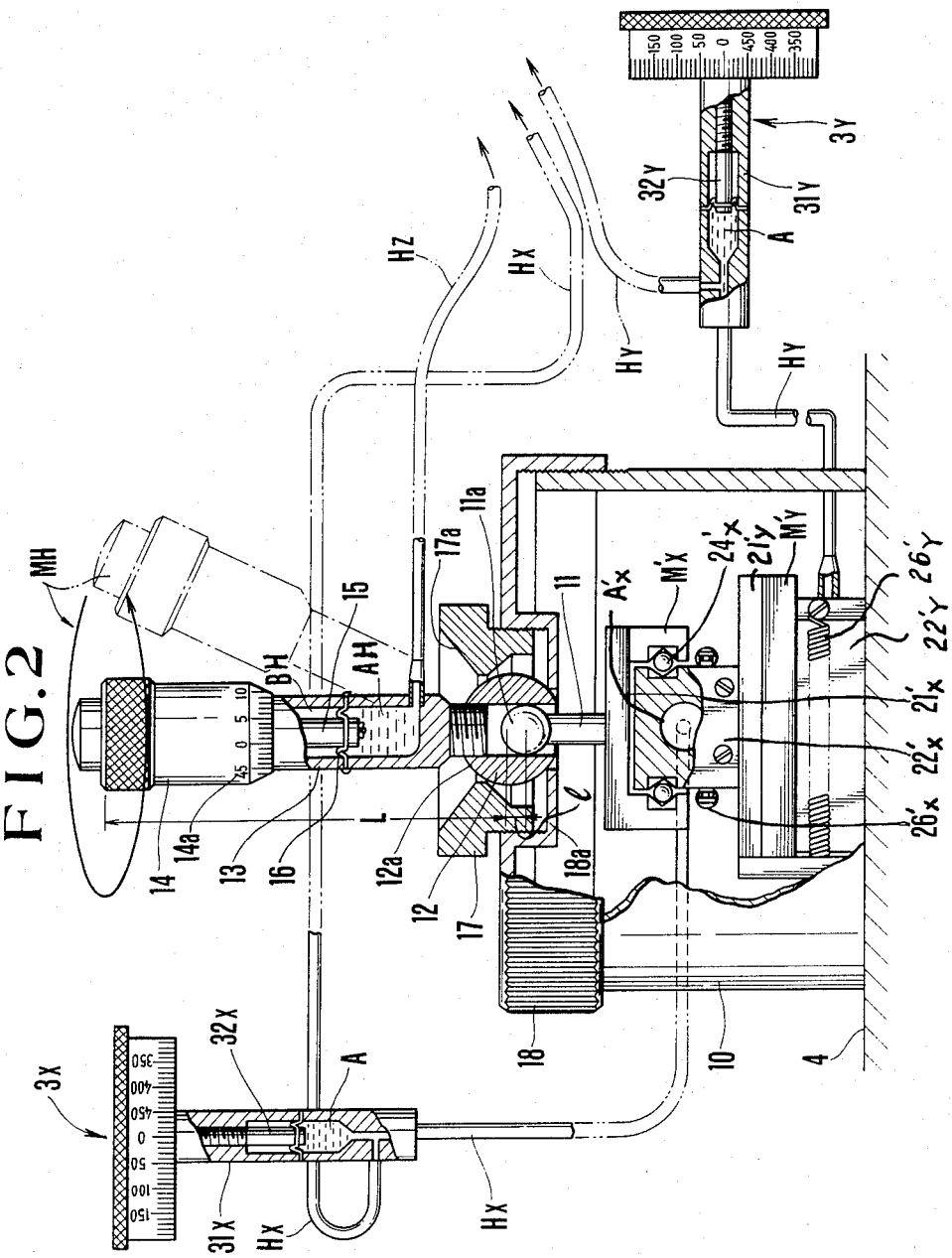
FIG. 2 is a partially sectioned front view of two fine adjusting devices incorporated in the fine controlling system of the invention, shown in an enlarged scale.

In FIG. 2 reference numeral 10 designates a cylindrical box to accomodate the parts and members in the hydraulic system arranged on a table 4. Reference letter $M_x'$ designates a master actuator adapted to operate in the direction of the X coordinate, whereas reference letter $M_y'$ designates a master actuator adapted to operate in the direction of the Y coordinate. As is apparent from drawing FIG. 2, the master cylinder member $22_x'$ of the actuator $M_y'$ in the Y-coordinate is fixedly mounted on the table 4, whereas the cylinder member $22_x'$ of the master actuator $M_x'$ in the X-coordinate is fixedly mounted on the slide $21_y'$ of the actuator $M_y$ in the Y-coordinate extending at a right angle relative to the former. Thus, the slide $21_y$ of the master actuator $M_y'$ moves reciprocably in the direction of Y-coordinate and the slide $21_x'$ of the master actuator $M_x'$ moves reciprocably in the direction of X-coordinate. The members constituting the master, actuators $M_x'$ and $M_y'$ in the fine adjusting device MH are constructed in a similar manner as described above with respect to slave cylinders $M_x$, $M_y$ and $M_z$ in FIGS. 3(a) and (b). In FIG. 2 reference numerals $26_x'$, $26_x'$ designates an expansive coil spring and reference numeral $24_x'$, $24_x'$ designates a steel ball for actuators $M_x'$, $M_y'$, respectively.

Further, reference numeral 11 designates a support rod standing upright on the slide 21 of the master actuator $M_x'$. A ball $11_a$ is fixedly secured to the upper end part of the support rod 11. Reference numeral 12 designates a movable ball which has a through hole $12_a$ having inner diameter dimensioned appreciable larger than the diameter of the ball $11_a$ so that the latter is fitted into the through hole $12_a$ of the ball 12 with a certain clearance maintained therebetween. Thus, the movable ball 12 can be freely rotated about the stationary ball $11_a$ by an angular extent of 360 degrees as seen from above.

The through hole $12_a$ of the movable ball 12 is formed with female threaded portion at its upper end part so that a sleeve casing 13 of the fine adjusting device MH is attached to the movable ball 12 by screwing the male threaded portion of the sleeve casing 13 into the female threaded portion of the movable ball 12. Further, the sleeve casing 13 has a micrometer head 14 rotatably fitted onto its upper part, the micrometer head 14 including a knurled handle with a number of calibrations $14_a$ engraved on the lower end periphery thereof. In the illustrated embodiment the handle of the micrometer head 14 has 250 calibrations so that a screw spindle 15 serving as a piston rod is moved downward or upward by a distance of 500 microns when the micrometer head 14 is operated by one revolution. The screw spindle 15 is operatively connected to the male threaded portion of the handle. Thus, one calibration on the micrometer head 14 represents a movement of the screw spindle 15 by a distance of 2 microns. As is apparent from the drawing, a flexible diaphragm 16 is fitted to the lower end part of the screw spindle 15 in the same manner as the flexible diaphragm $27_x'$, $27_y'$, $27_z'$ is fitted in the slave $M_x$, $M_y$ and $M_z$ so as to divide the inside space of the sleeve casing 13 into two parts comprising a hydraulic chamber AH and an empty chamber BH. Thus, when the micrometer head 14, (i.e., the screw spindle 15) is rotated by one revolution, a volume of hydraulic oil equivalent to a distance of 2 microns is displaced while deflecting the diaphragm 16. It will be readily understood from the above description that among the aforesaid three slave actuators $M_x$, $M_y$ and $M_z$ the slave actuator $M_z$ is adapted to undertake control operation in the direction the Z-coordinate and is adjusted by means of the fine adjusting device MH.

Further, description will be made in more details with respect to the fine adjusting device MH. A tightening bush 17 with an inside conical surface 17a formed thereon is screwed into the female threaded portion of a turn table 18 in such a manner as to come in contact with the spherical surface of the movable ball 12 without any hindrance given to swing movement of the entire fine adjusting device MH. A shown in the drawing FIG. 2, the turn table 18 is rotatably capped on the upper male threaded part of the cylindrical box 10 and includes a recess with the female threaded portion formed at the central part thereof so as to swingably carry the fine adjusting device MH. Thus, the movable ball 12 is tightened or loosened on the central recessed part of the turn table 18 by turning the tightening bush 17 in the required direction whereby swing movement of the fine adjusting device MH by an angular distance of 360 degrees as seen from the above can be carried out smoothly.

Next, description will be made as to the positional relation between the movable ball 12 and the stationary ball $11_a$. The height position of the center of the stationary ball $11_a$ does not change during operation of the system of the invention. As long as the height position of the center of the movable ball 12 is identical to that of the stationary ball $11_a$, any swing movement of the fine adjusting device MH causes no displacement of the master actuators $M_x'$ and $M_y'$. When the turn table 18 is turned in the required direction so as to displace the entire fine adjusting device MH up or down, there is developed a difference in the height between the position of the center of the stationary ball $11_a$ and that of the movable ball 12. As center distance l increases, swing movement of the fine adjusting device MH causes the masten actuators $M_x'$ and $M_y'$ to be simultaneously displaced in the directions of two coordinates. Assuming that variable length measured from the center of the movable ball 12 to the uppermost end of the holder on the fine adjusting device MH is represented by L, dimensional ratio l/L is displayed, for instance, in the form of 1:300 along the whole periphery of the turn table 18. Thus, by selectively determining the above dimensional ratio each time the system operates, a scope of examination of cell structure with the use of a glass electrode can be enlarged or reduced as required.

Next, description will be made as to operational relation between the control stand M with the glass electrode P carried thereon and the fine adjusting device MH.

The hydraulic chamber $A_x$ of slave actuator $M_x$ in the direction of X-coordinate on the control stand M is in communication with the hydraulic chamber $A_x'$ of the master actuator $M_x'$ in the cylindrical box 10 via a hydraulic hose $H_x$. The hydraulic chamber $A_y$ of slave actuator $M_y$ in the direction of Y-coordinate on the control stand M is in communication with the hydraulic chamber $A_y'$ (not shown in FIG. 2) of the master actuator $M_y'$ in the cylindrical box 10 via a hydraulic hose $H_y$. The hydraulic chamber $A_z$ of slave actuator $M_z$ in the direction of Z-coordinate on the control stand M is in communication with the hydraulic chamber AH in the sleeve casing 13 of the fine adjusting device MH via a hydraulic hose $H_z$. Specifically, both the hydraulic chambers $A_x$, $A_y$ in the cylinders $22_x, 22_y$ of the slave actuators $M_x$ and $M_y$ in which petroleum based hydraulic oil 28 is filled with no air foam included therein are in operative association with chambers $A_x', A_y'$ of master actuators $M_x'$ and $M_y'$, respectively, by means of hoses $H_x$ and $H_y$ made of teflon or the like material extending therebetween. The hydraulic chamber A in the sleeve casing 13 of the fine adjusting device MH is in communication with the hydraulic chamber A of the actuator $M_z$ in the direction of Z-coordinate with the aid of hose $H_z$ extending therebetween.

Further, a fine adjusting handle 3X is disposed at a predetermined position located midway of the hydraulic hose $H_x$ communicating the master actuator $M_x'$ in the direction of X-coordinate. Another fine adjusting handle 3Y is disposed at a predetermined position located midway of the hydraulic hose $H_y$ communicating the master actuator $M_y'$ and slave actuator $M_y$ in the direction of Y-coordinate. As is apparent from FIG. 2, the fine adjusting handles 3X and 3Y include a cylinder member as identified with reference numeral 31X and 31Y in which a hydraulic chamber A is formed in the same manner as that in the fine adjusting device MH. Each of the fine adjusting handles 3X and 3Y is designed so that a screw spindle 32X or 32Y moves forward by a distance of 500 microns at every time when the handle is rotated by one revolution, and therefore one calibration engraved on the periphery of the handle represents movement of the screw spindle 32X or 32Y by a distance of 1 micron. In FIG. 2 both the fine adjusting handles 3X and 3Y are schematically illustrated in the form of a piping diagram and in practice they are located in the proximity of the fine adjusting device MH so as to constitute a compact assembly unit.

Description will be made further as to operational relationship between the fine adjusting device MH on the control stand M and the fine adjusting handles 3X and 3Y. These three essential components constituting the system of the present invention are in operative connection with the slave actuators $M_x$, $M_y$, and $M_z$ on the control stand M via hydraulic hoses $H_x$, $H_y$ and $H_z$, respectively, in such a manner that movement of the glass electrode P, i.e., displacement of the control stand M is roughly adjusted by manually operating the fine adjusting handles 3X and 3Y. Electrode P is then precisely adjusted in the three directions of X-, Y- and Z-coordinates simultaneously by operating the fine adjusting device MH.

Next, operation of the system of the invention will be described below.

Rough adjustment is first carried out by turning the fine adjusting handles 3X and 3Y with the aid of both hands of an operator. Then, fine adjustment is carried out in the directions of three coordinates, as required by operating the fine adjusting device MH. Specifically, as the micrometer head 14 is rotated by a predetermined angular distance in the required direction, the screw spindle 15 serving as a piston rod is displaced downward to deflect the diaphragm 16 attached to the lower end part thereof whereby hydraulic oil in the hydraulic chamber AH is compressed. Increased hydraulic pressure is transmitted to the slave actuator $M_z$ via hose $H_z$ and thereby the slave actuator $M_z$ is caused to move corresponding to the displacement of the screw spindle 15. Thus, the glass electrode P is displaced by a required distance in the direction of Z-coordinate. It should of course be understood that piror to operations as described above a dimensional ratio l/L is previously set to a predetermined value.

Further, as the micrometer head 14 is caused to swing with the handle grasped by operator's fingers, the master actuators $M_x'$ and $M_y'$ in the cylindrical box 10 are displaced in both the directions of X- and Y-coordinates by a very short distance corresponding to the angular distance of swing movement of the micrometer head 14.

Fine displacement of the master actuators $M_x'$ and $M_y'$ as described above is transmitted to the slave actuators $M_x$ and $M_y$ on the control stand M with glass electrode P mounted thereon via hydraulic hoses $H_x$ and $H_y$ whereby the glass electrode P is displaced by a required distance in the directions of X- and Y-coordinates.

During actuation of the respective actuators, for example, master actuator $M_x'$ the slide $21_x'$ moves against resilient force of the coil springs $26_x'$ disposed at both the sides thereof and thereby hydraulic pressure in the hydraulic chamber $A_x'$ increases while the slide $21_x'$ is maintained in a stable state without any fluttering in the transverse direction owing to the arrangement of the balls $24_x'$ and the coil springs $26_x'$. Thus, the slide $21_x'$ is firmly held by means of the rod $29_x'$ under the influence of resilient force of the coil springs $26_x'$, even when operator's fingers are disengaged from the micrometer head 14 for any reason after the glass electrode P is inserted into a certain cell structure. As a result it is assured that an occurrence of malfunction such as disconnection of glass electrode P from cell or the like is prevented. Actuation of the other master actuator $M_y'$ and the slave actuators $M_x$, $M_y$ and $M_z$ are similar as described above for master actuator $M_x'$.

Thus, the fine control system of the invention assures that a glass electrode P is precisely inserted into a cell at a predetermined position thereof by displacing the glass electrode P by a required distance in the directions of X-, Y- and Z-coordinates merely with one hand operation of the fine adjusting device MH whereby an intended examination work can be carried out.

As will be readily understood from the above description, a glass electrode P can be precisely displaced by a required distance simultaneously in the directions of three coordinates merely with one hand operation of the fine adjusting device MH after rough positional adjustment is carried out with both hands operation. Moveover, operations in the control system are performed in quick response at a high speed without any fear of disconnection of glass electrode P from the cell structure.

While the present invention has been described above only with control operations for a glass electrode, it should be of course understood that application of the invention should not be limited only to glass electrode but it may be applied to other tool or device such as micropipette, micro surgical knife or the like, each of which requires fine and precise control.

What is claimed is:

1. A system for finely and precisely controlling the position of a glass electrode or the like comprising:
   a control stand for locating the glass electrode or the like as required in the directions of X-, Y- and Z-coordinates, said control stand including first, second and third actuator means mounted on said control stand for respectively actuating the glass electrode or the like in the directions of the X-, Y- and Z-coordinates, each said first, second and third actuators including a cylinder member and a slide,
   first fine adjusting means operatively connected to said first and second actuator means for roughly adjusting said first actuator means and said second actuator means to responsively roughly adjust said glass electrode or the like in the X- and Y-coordinates, respectively, said rough adjustment being effected with both hands operation of an operator,
   second fine adjusting means operatively connected to said first, second and third actuator means for (a) adjusting said third actuator means to responsively finely adjust said glass electrode of the like in the Z-coordinate and for finely adjusting said first and second actuator means to responsively finely adjust said glass probe or the like in the X-coordinate and the Y-coordinate, respectively with one hand operation of the operator, and
   hose means for establishing operative hydraulic communication between the control stand, the first fine adjusting means and the second fine adjusting means.

2. A system for finely and precisely controlling the position of a glass electrode or the like as in claim 1, wherein the control stand further includes:
   a base,
   a holder arm standing upright on the base,
   Z-coordinate slave actuator means fixedly mounted to said holder arm to actuate the glass probe or the like in the vertical direction,
   Y-coordinate slave actuator means fixed to said Z-coordinate slave actuator means to actuate the glass probe or the like in the horizontal direction at a right angle relative to the direction of actuation of the Z-coordinate slave actuator means,
   X-coordinate slave actuator means fixedly mounted on said Y-coordinate slave actuator means to actuate in the horizontal direction at a right angle relative to the dirction of actuation of the Y-coordinate slave actuator means, and
   adjustable holding means removably disposed on said X-coordinate slave actuator means to adjustably hold said glass electrode or the like so that said glass electrode or the like extends in the horizontal direction.

3. A system for finely and precisely controlling the position of a glass electrode or the like as in claim 1, wherein the first fine adjusting means includes a first fine adjusting handle device in operative connection with the X-coordinate slave actuator means on the control stand via said hose means, and a second fine adjusting handle device in operative connection with the Y-coordinate slave actuator means via said hose means and wherein said second fine adjusting means includes a first master hydraulic chamber and a second master hydraulic chamber, each of said first and second fine adjusting handle devices including:
   a cylinder member having an end wall,
   a rotatable handle with a number of calibrations engraved on the periphery thereof,
   screw spindle means reciprocally moveable in the cylinder member in response to rotation of said handle,
   said screw spindle means having a flexible diaphragm means fixedly secured to said screw spindle means, and a hydraulic chamber defined between the diaphragm means and the end wall of the cylinder member, said hydraulic chamber being in hydraulic communication with a respective one of said first and second actuator means of the control satnd via said hose means and in communication with a respective one of said first and second master hydraulic chambers of said second fine adjusting device via said hose means.

4. A system for finely and precisely controlling the position of a glass electrode or the like as defined in claim 3, wherein the second fine adjusting means includes Y-coordinate master actuator means for actuating said glass probe or the like in the horizontal direction, X-coordinate master actuator means fixedly mounted on the Y-coordinate master actuator means to actuate said glass probe or the like in the horizontal direction at a right angle relative to the direction of actuation of the Y-coordinate actuator, a support rod, a stationary ball at the uppermost end of the support rod, a movable ball having a through hole formed therein in the vertical direction so as to contain said stationary ball with a certain clearance maintained therebetween, said movable ball being turnable through 360 degrees relative to horizontal inclinable by a certain angle relative to vertical, said movable ball defining a female threaded part, and a micrometer head means having a male threaded part threadably connected to said female threaded part of the through hole of the movable ball, said X-coordinate master actuator means in operative hydraulic communication with the first actuator means of the control stand via said hose means and wherein the first fine adjusting handle device is disposed therebetween, said Y-coordinate master actuator means in operative hydraulic communication with the second actuator means of the control stand via said hose means and wherein the second fine adjusting handle device is disposed therebetween.

5. A system for finely and precisely controlling the position of a glass electrode or the like as in claim 4, wherein the micrometer head means includes a sleeve casing defining a threaded part formed at a lower end part thereof and an end wall, a rotatable micrometer head with a number of calibrations engraved on the periphery thereof, screw rod means displaceable in the vertical direction in response to rotation of said micrometer head, said screw rod means having a flexible micrometer diaphragm fixedly secured thereto, and a micrometer hydraulic chamber defined between the micrometer diaphragm and the end wall of the sleeve casing, said micrometer hydraulic chamber being in communication with said third actuator means of the control stand via said hose means, and means to mount the micrometer head means for rotation and inclination about a center of the movable ball within a predetermined extent so that an assembly of the first actuator means and the second actuator means is finely adjusted by means of the support rod having the stationary ball attached thereto, said micrometer head means for transmitting variation in hydraulic pressure in both the X- and Y-coordinate master actuator means to the first actuator means and the second actuator means, respectively, on the control stand via said hose means so as to finely control said glass electrode or the like as required.

6. A system for finely and precisely controlling the position of a glass electrode or the like as defined in claim 5, further comprising a cylindrical box, a turn table carrying said micrometer head means and including means to mount said turn table onto the cylindrical box to permit adjustment of the height of said turn table in response to turning movement of said cylindrical box to thereby effect a variation in the height difference between the center of the movable ball and the center of the stationary ball to responsively vary the inclination of the micrometer head means.

7. A system for finely and precisely controlling the position of a glass electrode or the like as defined in claim 5, wherein the turn table includes a recess having a female threaded part formed at the central area thereof, and a tightening bush means having male threaded part screwed into the female threaded part of said recess so as to rotatably contain the movable ball in a space defined therebetween, said bush means for selectively determining pivotal movement of said micrometer head means.

8. A system for finely and precisely controlling the position of a glass electrode or the like as defined in claim 1, wherein each of the first, second and third actuator means mounted on the control stand to locate the glass electrode or the like in the directions of X-, Y- and Z-coordinates, respectively, includes a slide having an inverted U-shaped cross-sectional configuration, a cylinder member disposed in said slide so as to move in the longitudinal direction, a rod fixedly secured to one end of the slide to protrude into an interior of the cylinder member in the axial direction, a flexible diaphragm fixedly secured to a fore end part of said rod and liquid-tightly attached to an inner wall of the cylinder member, and a hydraulic chamber defined between the diaphragm and an end wall of the cylinder members, said first, second and third actuator means varing hydraulic pressure in the hydraulic chamber in response to expansion or contraction of said diaphragm so that the slide moves back and forth relative to the cylinder member.

9. A system for finely and precisely controlling the position of a glass electrode or the like as defined in claim 8, wherein the slide includes inner slide walls and first rails firmly embedded into the inner slide side walls thereof, said first rails being formed with a first V-shaped groove, and wherein the cylinder member includes outer side walls and second rails firmly embedded into the outer side walls thereof, said second rails being formed with a second V-shaped groove, each said second groove positioned opposite to a respective one of and a number of balls positioned in the space defined between the first and second grooves.

10. A system for finely and precisely controlling the position of a glass electrode or the like as defined in claim 8, wherein each said first, second and third actuator means includes, a bracket, a pair of coil springs disposed between the bracket and the slide member, said coil springs under tension so that the slide is biased against resilient force of the coil springs.

* * * * *